United States Patent [19]

Portnoy

[11] Patent Number: 4,838,682
[45] Date of Patent: Jun. 13, 1989

[54] OCULAR TOPOLOGY SYSTEM
[75] Inventor: Vladimir Portnoy, Irvine, Calif.
[73] Assignee: Allergan, Inc., Irvine, Calif.
[21] Appl. No.: 172,948
[22] Filed: Mar. 23, 1988

Related U.S. Application Data

[63] Continuation of Ser. No. 859,470, May 5, 1986, abandoned.

[51] Int. Cl.$^4$ .............................................. A61B 3/10
[52] U.S. Cl. .................................... 351/212; 351/211
[58] Field of Search ............... 351/206, 211, 212, 214

[56] References Cited

U.S. PATENT DOCUMENTS 4,019,813  4/1977  Cornsweet et al. .
4,046,463  9/1977  La Russa et al. .
4,165,744  8/1979  Cravy et al. .
4,440,477  4/1984  Schachar .

Primary Examiner—Rodney B. Bovernick
Assistant Examiner—P. M. Dzierzynski
Attorney, Agent, or Firm—Weissenberger & Peterson

[57] ABSTRACT

Topological information of the cornea and anterior chamber of an eye is optically developed by projecting toward said eye a target image sharply focused in a movable flat plane. As the plane is moved through the eye, the reflection of the target is in focus first at the center and then at increasingly radially outward locations. The reflection is detected and clipped to delete all image portions which are out of focus. As the image plane is moved through the eye, the clipped reflection traces the topology of the eye. This information can be fed into a computer and used to compute appropriate topological displays. Such computations can readily be made insensitive to any eye movement during the measuring process.

15 Claims, 4 Drawing Sheets

OCULAR TOPOLOGY SYSTEM

STATEMENT OF RELATED CASE

This application is a continuation of application Ser. No. 859,470 filed May 5, 1986 now abandoned and also entitled "Ocular Topology System".

FIELD OF THE INVENTION

This invention relates to a method and apparatus for accurately measuring the topography of a cornea, and more particularly, to a method in which topographical information is obtained by moving the image position of a target projected towards the cornea and detecting the in-focus portions of the image as its position is moved.

BACKGROUND OF THE INVENTION

In preparation for corneal surgery such as is commonly used for vision correction, it is necessary for the surgeon to have highly accurate information concerning the shape and thickness of the cornea throughout its surface. It has been conventional in the past to measure the contour and thickness of the cornea by optically or ultrasonically examining the cornea at a number of distinct points on its surface. The problem with this approach is that since the cornea is often quite irregular in shape and thickness, unappreciated variations in the measured parameters may occur between the measuring locations, and it is consequently possible that damage to the cornea may occur in surgery due to cuts of excessive or insufficient depth. Another problem arises from the fact that the cornea can move during the examination, and it is therefore difficult to correlate the various locations at which measurements are being taken in sequence.

It is therefore desirable to provide a method by which the contour and thickness of the cornea can be measured on a substantially continuous basis and in a manner in which eye movement during the measuring process is of little or no consequence.

SUMMARY OF THE INVENTION

The invention solves the above-stated problems by projecting onto the cornea a target image which is focused in an image plane (or, more generally, an image surface of known curvature) with a very shallow depth of field. The reflection of the target image from the cornea is observed by an autocollimating video camera whose sensitivity is so adjusted as to register only those portions of the target image which are sharply in focus.

As the image plane of the inventive device is moved toward the cornea, a dot image will appear in the center of the screen when the image plane first contacts the epithelium of the cornea. As the image plane is moved further toward the eye, a gradually outwardly moving ring of dot images will appear on the screen. Eventually, as the image plane reaches the endothelium of the cornea, a new dot image will appear on the screen, and a second set of outwardly moving dot images will appear on further movement of the image plane.

By correlating the position of the image plane with the distance of the dot images from the center of the screen on a continuing basis, a mathematical expression can be generated which exactly defines the contours of both the epithelium and endothelium of the cornea, as well as the thickness of the cornea itself. It should be noted that in this procedure, a movement of the cornea will produce a simultaneous displacement of all the dot images in the direction of the movement. This simultaneous displacement can readily be compensated for by well-known electronic software/hardware techniques.

In addition to measuring the contour and thickness of the cornea, the inventive method can be used to calculate a three-dimensional representation of the anterior chamber of the eye by continuing to move the focal plane of the target image until it reaches the iris.

It is therefore the object of the invention to provide an optical method of continuously measuring the topography of a cornea simultaneously throughout its surface.

It is a further object of the invention to accomplish the foregoing result by tracking the reflections of a target image as the image plane of the target image is moved through the cornea.

BRIEF DESCRIPTION OF THE DRAWINGS

FIG. 3b illustrates the dot image seen on the television screen when the focal plane is in the position of FIG. 3a;

FIG. 4b illustrates the shift in the circular dot images as the image plane is moved between the positions shown in FIG. 4a;

FIG. 5b illustrates the dot image seen on the television screen when the focal plane is in the position of FIG. 5a.

DESCRIPTION OF THE PREFERRED EMBODIMENT

Figure 1:
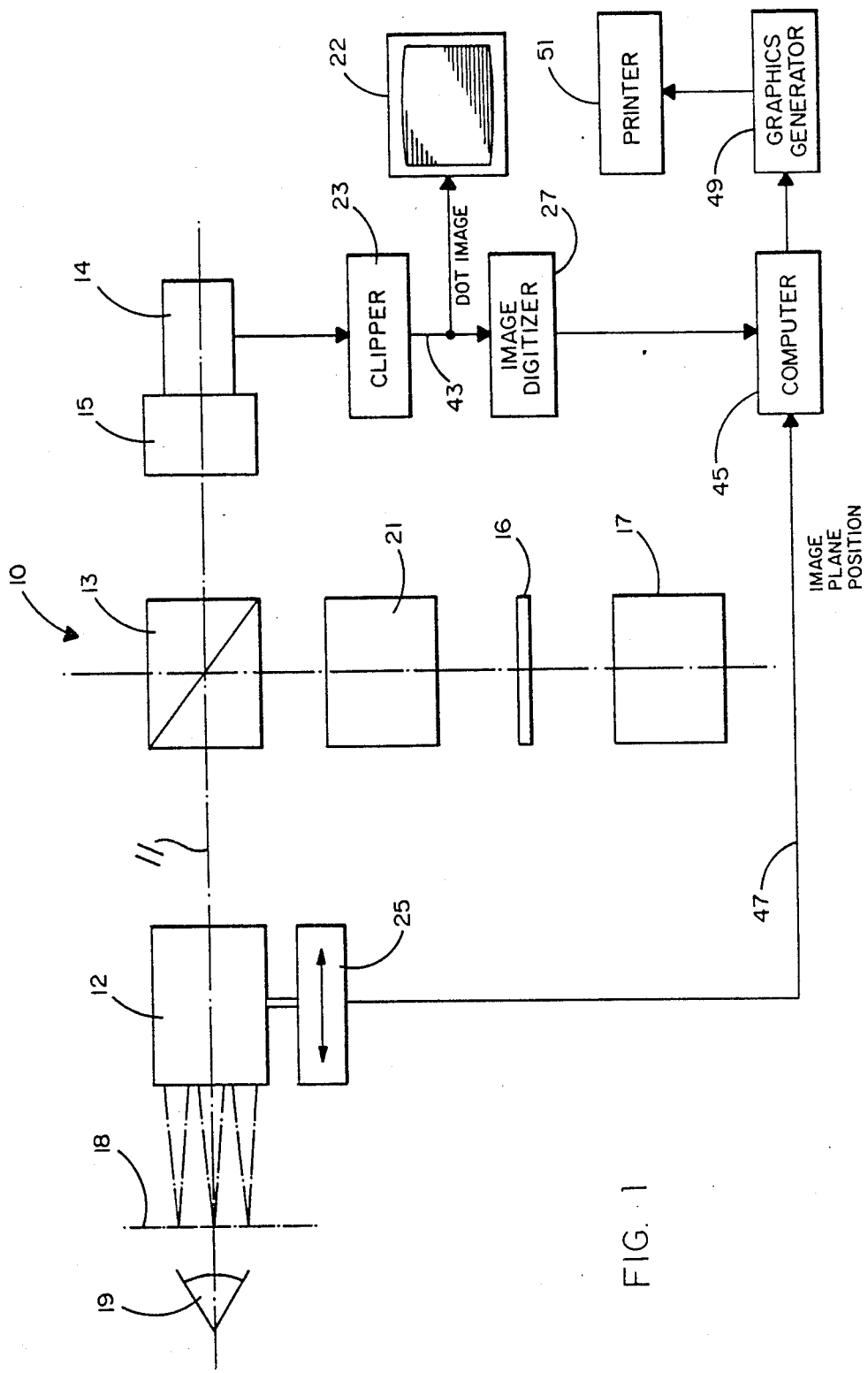
FIG. 1 is a schematic representation of the device of this invention.

FIG. 1 shows an optical system 10 including a focusing objective 12, a beam splitter 13 and a video camera 14 provided with an appropriate objective 15. An image of a target 16 illuminated by an illuminator 17 is projected toward the eye 19 through collimating optics 21, beam splitter 13, and focusing objective 12. The focusing objective 12 produces a sharply focused image of the target 16 in the image plane 18 which, as is clearly apparent in FIG. 1, is perpendicular to the direction of projection toward the eye 19 as defined by the X-axis or projection axis 11. The elements of the optical system 10 are so chosen, in accordance with known optical principles, to give the image plane 18 a very shallow field depth. As a result, the image of target 16 is sharp in the image plane 18, but becomes substantially blurred at even a very small distance in front of and behind image plane 18.

Reflections of the target image from the eye 19 are conveyed through focusing objective 12 and beam splitter 13 to the objective 15 of the video camera 14. Thus, the camera 14 sees the reflection of the target 16 in the eye 19.

In the preferred embodiment of the invention, the focusing objective 12 is movable in a horizontal direction in FIG. 1, toward and away from eye 19, by a stepping motor 25. The position of motor 25 is digitally encoded by conventional means into a position signal 47, which is transmitted to the computer 45 for a purpose described below. Alternatively, the focusing objective 12 may be fixed, and the target 16 may be movable.

In either event, in the position of image plane 18 shown in FIG. 1, the reflection of the target 16 by the eye 19 will be blurred. In accordance with the invention, the video output of camera 14 is electronically clipped by conventional clipping circuitry 23 so that only those portions of the reflected target image which are sharply in focus (and which therefore have the highest intensity) are transmitted by the clipper 23. Consequently, in the position of image plane 18 shown in FIG. 1, there is no video output from clipper 23.

When the actuation of the motor 25 moves the image plane 18 toward the eye 19 in FIG. 1, the image plane 18 will eventually contact the eye 19, and at least a portion of the target 16 will be reflected in sharp focus. That reflection is seen by the camera 14, passed by the clipper 23, and applied as the image through a conventional image digitizer 27 as the image input to computer 45 for contour mapping purposes.

Figure 2:
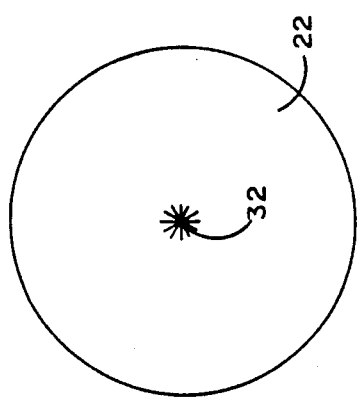
FIG. 2 illustrates one possible type of target which may be used in the preferred embodiment of the invention.

As shown in FIG. 2, the target 16 may preferably consist of a two-dimensional figure such as lines 24 radiating in all directions from a central point 26; however, other target configurations may be used to accommodate various algorithms which may be used in interpreting the moving dot images hereinafter described.

Figure 3B:
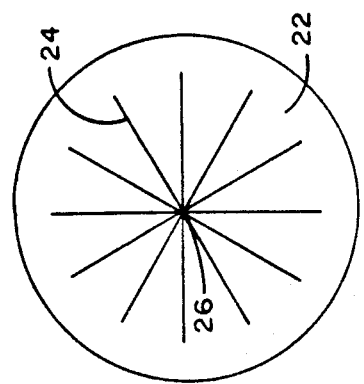
Figure 3A:
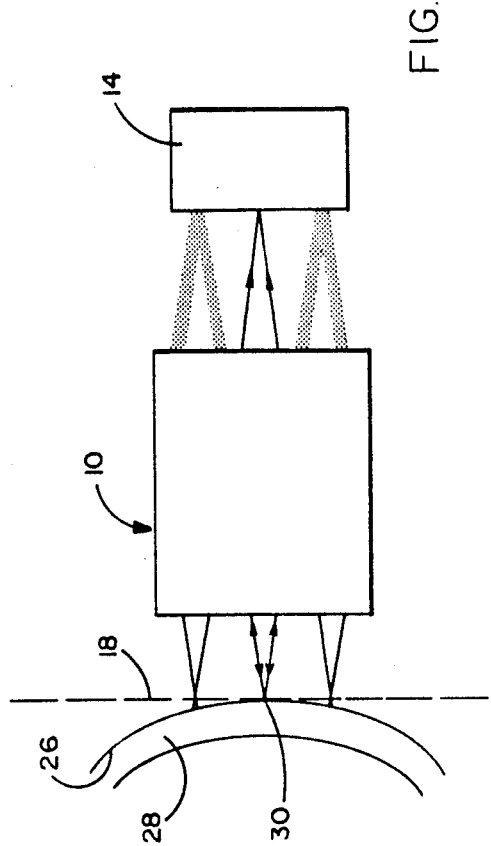
FIG. 3a is a schematic representation of the apparatus of this invention in a position where the focal plane first contacts the epithelium of the cornea.

Turning now to FIGS. 3a and 3b, it will be seen that when the apparatus of this invention is placed in front of the curved surface of a cornea and is moved toward the interior of the eye, the image plane 18 will first contact the epithelium 26 of the cornea 28 at a central point 30. Due to the curvature of the epithelium 26, all portions of the target image except the portion reflected from point 30 will be out of focus, and will therefore be clipped out by the clipper 23. As a result the image seen by computer 45 and by the monitor 22 will look as depicted in FIG. 3b when the apparatus is in the position of FIG. 3a. The dot 32 seen on the monitor 22 in this position is a representation of the center 26 of the target 16.

As the image plane 18 is moved toward the interior of the eye, point 30 will go out of focus, and a ring of locations including points 34 and 36 will come into focus. At the output of clipper 23, this translates into a ring of dots representing portions of the lines 24 of the target. The position of the dots in the ring including points 34 and 36 is an indication of the position of the epithelium 26 when the image plane is in the rightmost position of FIG. 4a. If the cornea is not spherical (as in the case of astigmatism), the locus of the dots will be oval rather than circular.

Figure 4A:
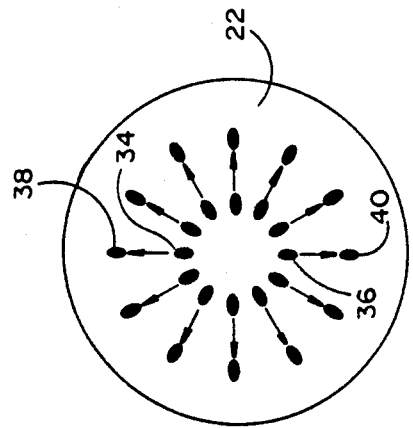
FIG. 4a illustrates the shift of the image as the focal plane moves toward the interior of the eye.
Figure 4B:
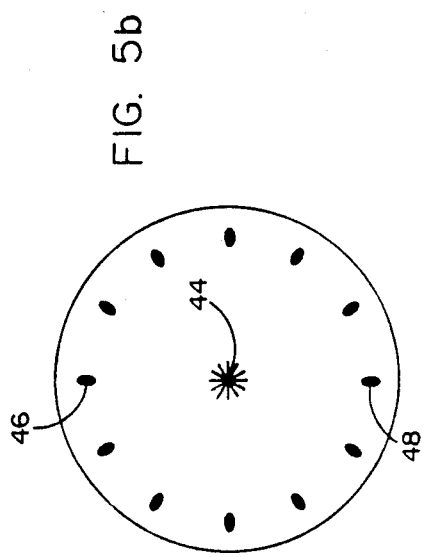

As the image plane 18 moves to the leftmost position in FIG. 4a, points 34 and 36 go out of focus and points 38, 40 come into focus. The dot image 43 now applied to computer 45 and produced on the monitor 22 is again a circle of dots, but now farther outward from the center of the screen than was previously the case.

Figure 5A:
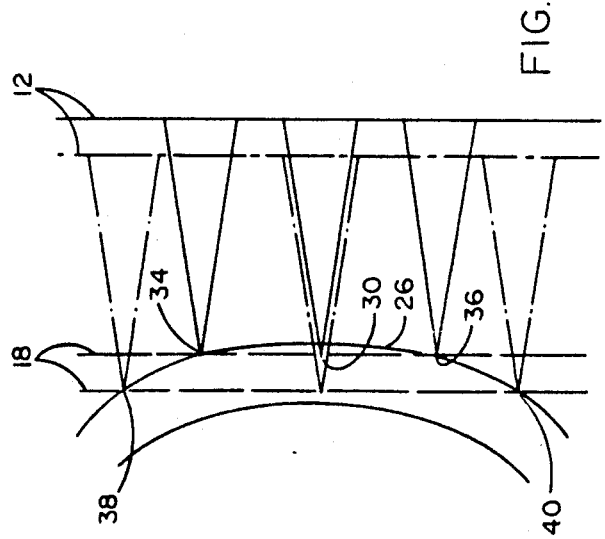
FIG. 5a illustrates the reflection from the endothelium when the center of the focal plane has reached the interior surface of the cornea.
Figure 5B:
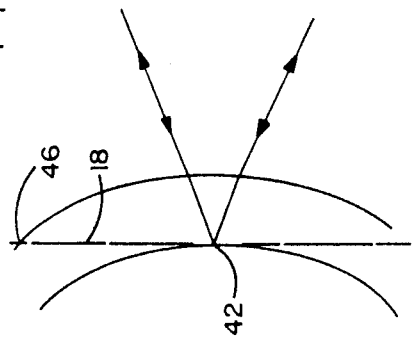

As the image plane 18 moves farther to the left, it will eventually hit the endothelium as shown in FIG. 5a. This second reflection will appear, as shown in FIG. 5b, as a second central dot 44 in the center of the still existing dot ring from points 46, 48. Continued movement of the image plane 18 to the left will then produce another ring of dots radiating out from the central dot 44 as the central dot 44 disappears.

Figure 6:
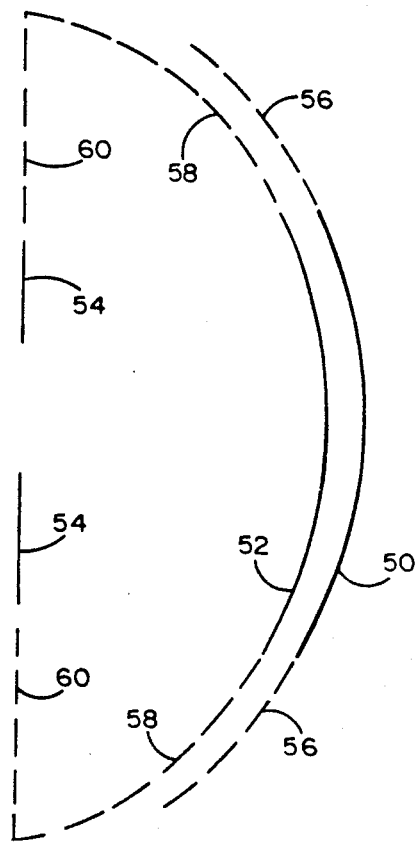
FIG. 6 represents the calculated representation of the cornea and anterior chamber when a full set of measurements have been taken.

The position of the dots in the digitized dot image scan by computer 45 can be analyzed within computer 45 by conventional techniques and can be correlated by the position input 47 with the position of the image plane 18 that produced them to provide the input to a conventional graphics generator 49 (FIG. 1). Knowing the coordinates of the dots in the dot image 43 and the corresponding position of the image plane 18, the computer 45 and graphics generator 49 can translate the image data at successive image plane positions into a three-dimensional or sectional representation of the cornea 28 in a format suitable for use by the surgeon. The output of the computer 45 may, for example, be used to produce a representation such as that of FIG. 6 on a printer 51 for any given sectional plane corresponding to one of the lines 24 of the target 16. In such a representation, the solid lines 50, 52 representing the cornea and 54 representing the iris may be actual measurements, whereas the dotted lines 56, 58 and 60 may be extrapolated from the measured lines 50, 52 and 54.

Eye movement during the mapping of the cornea does not interfere with the accuracy of the measurements in the apparatus of this invention. Whereas the progressive displacement of the image plane 18 causes the coordinates of the image dots to increase radially outwardly from a central point, eye movement causes all the dot coordinates to move in the same direction. This distinction is readily recognized by the computer 45, and allows it to disregard any dot shift caused by eye movement.

I claim:

1. A method for optically determining the topology of an eye, comprising the steps of:
    (a) projecting toward the eye a target image sharply focused in an image surface substantially perpendicular to the direction of projection;
    (b) moving said image surface through at least part of said eye;
    (c) detecting the in-focus portions of the reflection of said target image by surfaces of said eye; and
    (d) producing a representation of the location of said in-focus portions of said reflected target image with respect to a reference point for a plurality of positions of said image surface.

2. The method of claim 1, further comprising the step of:
    (e) using said representation to produce topological data for said eye.

3. The method of claim 2, further comprising the steps of:
    (f) monitoring the directions of movement of said in-focus target image portions as said image surface is moved; and
    (g) disregarding, for the purposes of producing said location representation, any movement of said image portions in which all of said image portions move in the same direction.

4. The method of claim 2, in which said topological data is a tomographic representation of said eye.

5. The method of claim 1, in which said target image is two-dimensional in said image surface.

6. An ocular topology device, comprising:

(a) optic means for projecting toward an eye a target image focused in an image surface of shallow field depth substantially perpendicular to the direction of projection, said image surface being movable toward and away from said eye;

(b) position sensing means for producing a signal representative of the position of said image surface;

(c) camera means for detecting the reflections of said target image by reflecting surfaces of said eye as said image surface is moved through said eye;

(d) clipping means for deleting from said target image reflections those image portions which are not sharply in focus; and (e) computer means connected to said position sensing means and said clipping means for storing the coordinates of the undeleted image portions with respect to a reference point in relation to successive positions of said image surface, and for producing therefrom information representative of the topology of said eye.

7. The device of claim 6, further comprising:

(f) movement selection means associated with said computer means for shifting said reference point to compensate for eye movement whenever all of said undeleted image portions move in the same direction.

8. The device of claim 6, in which said target image consists of lines radiating outwardly from a central point.

9. The device of claim 8, in which said central point is said reference point.

10. The device of claim 6, further comprising:

(g) display means associated with said computer means for displaying a representation of the topology of said eye computed by said computer means from said coordinates and image surface positions.

11. The device of claim 10, in which said representation is a tomographic representation.

12. The device of claim 6, in which said target image is two-dimensional in said image surface.

13. An ocular topology device, comprising:

(a) optic means for projecting toward an eye a target image focused in a flat plane substantially perpendicular to the direction of projection, said plane being movable toward and away from said eye;

(b) position sensing means for producing a signal representative of the position of said plane;

(c) camera means for detecting the reflections of said target image by reflecting surfaces of said eye as said plane is moved through said eye;

(d) clipping means for modifying those image portions which are not sharply in focus; and (e) display means for displaying said target image reflections.

14. The device of claim 13, in which said modification is a deletion, and said display means display only the undeleted portions of said target image reflections.

15. The device of claim 13, in which said target image is two-dimensional in said plane.

* * * * *